(12) United States Patent
Kim et al.

(10) Patent No.: US 10,405,832 B2
(45) Date of Patent: Sep. 10, 2019

(54) ULTRASOUND DIAGNOSIS APPARATUS AND METHOD

(71) Applicant: SAMSUNG MEDISON CO., LTD., Hongcheon-gun (KR)

(72) Inventors: Han-eol Kim, Hongcheon-gun (KR); Dong-hoon Oh, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 718 days.

(21) Appl. No.: 14/934,782

(22) Filed: Nov. 6, 2015

(65) Prior Publication Data

US 2016/0128672 A1 May 12, 2016

(30) Foreign Application Priority Data

Nov. 6, 2014 (KR) .................. 10-2014-0153737

(51) Int. Cl.
*A61B 8/00* (2006.01)
*A61B 8/08* (2006.01)
(Continued)

(52) U.S. Cl.
CPC ............ *A61B 8/5215* (2013.01); *A61B 8/463* (2013.01); *A61B 8/466* (2013.01); *A61B 8/469* (2013.01); *A61B 8/52* (2013.01); *A61B 8/54* (2013.01); *G06F 16/5862* (2019.01); *G06T 11/001* (2013.01); *G06T 15/04* (2013.01); *A61B 8/483* (2013.01); *G06T 2210/41* (2013.01)

(58) Field of Classification Search
CPC ....... A61B 8/5215; A61B 8/469; A61B 8/463; A61B 8/54; A61B 8/52; A61B 8/00; A61B 8/483; A61B 8/466
See application file for complete search history.

(56) References Cited

U.S. PATENT DOCUMENTS 5,249,263 A * 9/1993 Yanker ................ G06F 3/04845
345/594
6,254,540 B1 * 7/2001 Kikuchi ................... A61B 8/00
600/443

(Continued)

FOREIGN PATENT DOCUMENTS

JP 2013524284 A 6/2013
KR 1020070081802 A 8/2007
(Continued)

OTHER PUBLICATIONS

Communication dated Apr. 12, 2016, issued by the European Patent Office in counterpart European Application No. 15191842.2.

*Primary Examiner* — Joel Lamprecht
(74) *Attorney, Agent, or Firm* — Sughrue Mion, PLLC

(57) ABSTRACT

An ultrasound diagnosis apparatus includes: a controller configured to recognize an object included in an ultrasound image and search at least one piece of texture information corresponding to the recognized object; a display configured to display the ultrasound image and the searched at least one piece of texture information; a user interface configured to receive an input for selecting one piece of texture information from among the searched at least one piece of texture information; and an image processor configured to perform texture mapping of the selected piece of texture information onto at least one region in the ultrasound image of the object.

18 Claims, 15 Drawing Sheets

(51) Int. Cl.
*G06T 11/00* (2006.01)
*G06T 15/04* (2011.01)
*G06F 16/583* (2019.01)

(56) References Cited

U.S. PATENT DOCUMENTS

| | | |
|---|---|---|
| 2011/0184290 A1 | 7/2011 | Yoo et al. |
| 2012/0127200 A1* | 5/2012 | Kohara .................. G06T 15/08 |
| | | 345/629 |
| 2013/0065211 A1 | 3/2013 | Amso et al. |
| 2014/0187948 A1 | 7/2014 | Gerard et al. |

FOREIGN PATENT DOCUMENTS

| | | |
|---|---|---|
| KR | 1020110087355 A | 8/2011 |
| WO | 98/23210 A1 | 6/1998 |

\* cited by examiner

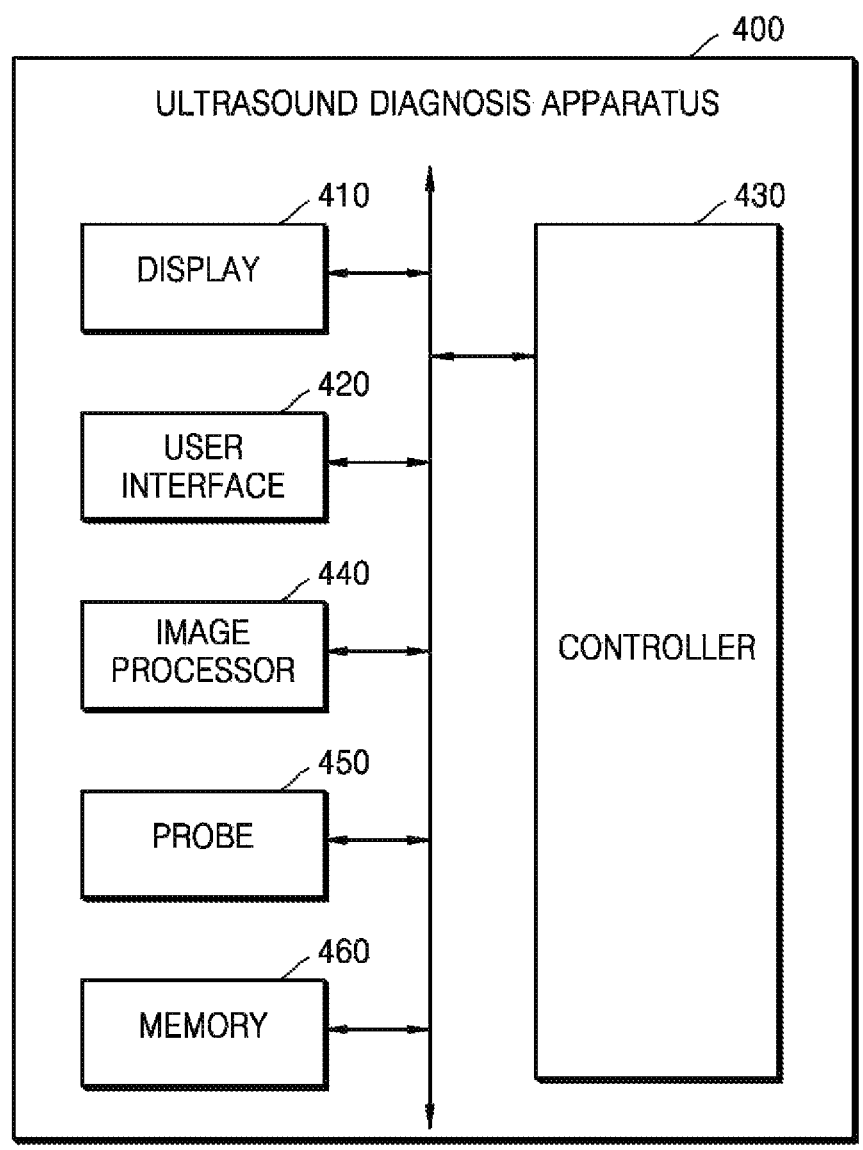

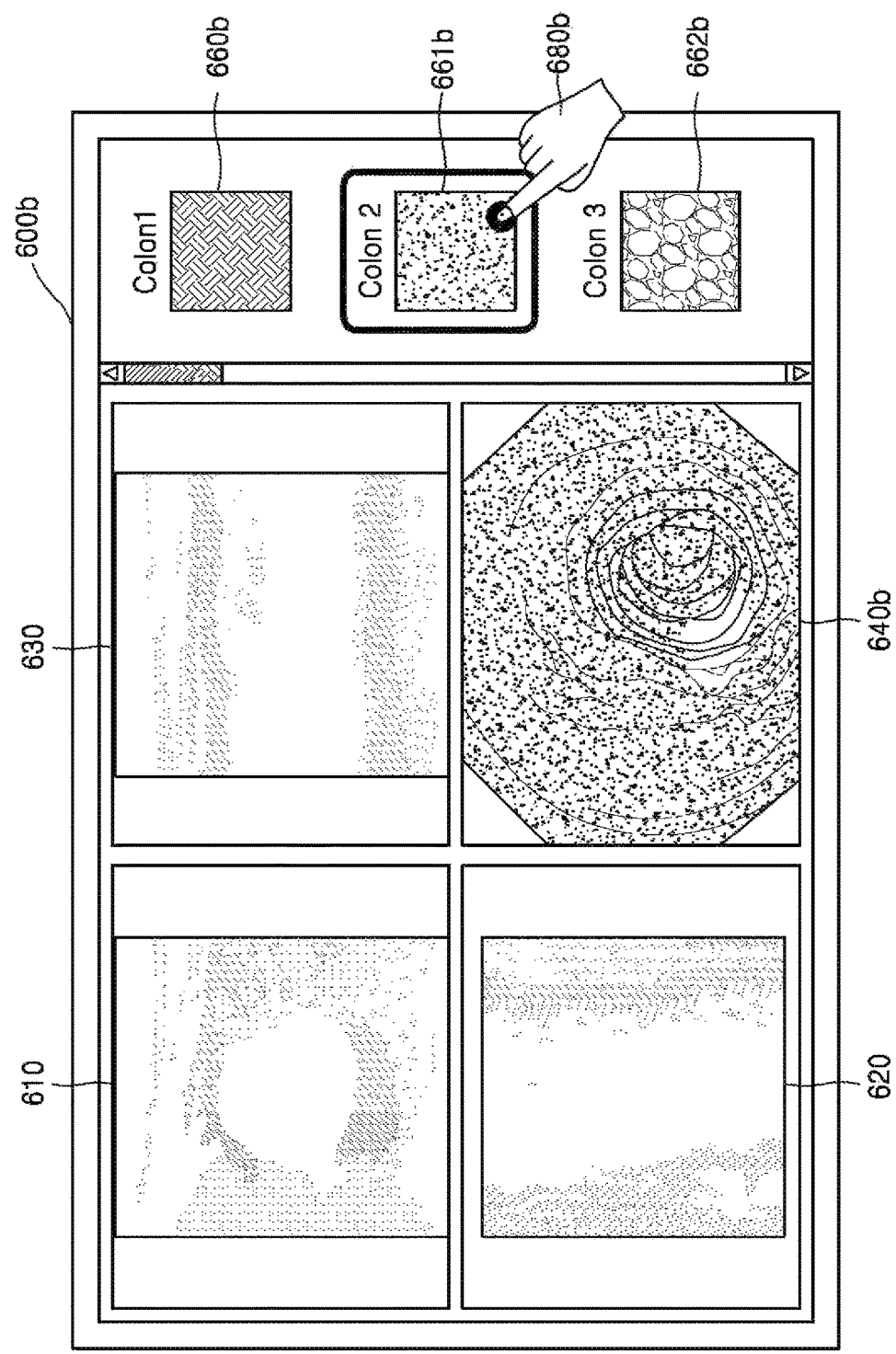

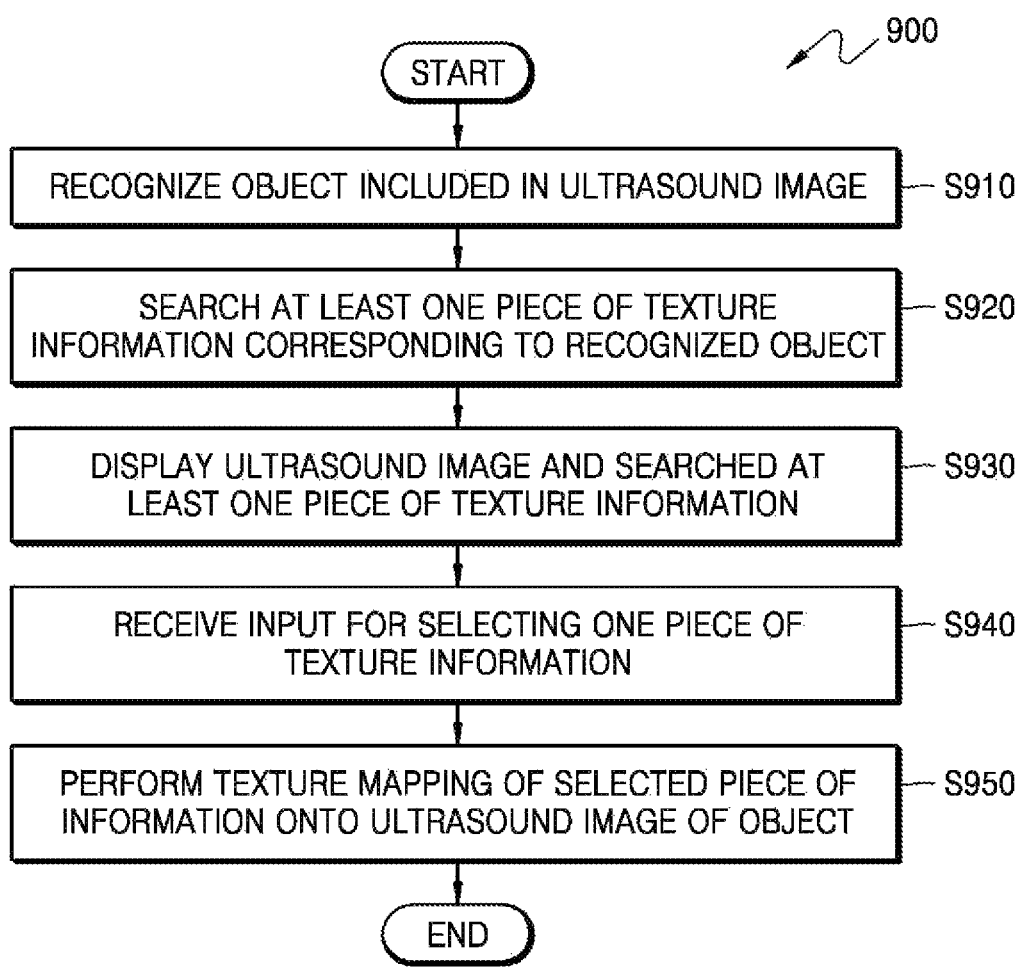

ULTRASOUND DIAGNOSIS APPARATUS AND METHOD

RELATED APPLICATION

This application claims the benefit of Korean Patent Application No. 10-2014-0153737, filed on Nov. 6, 2014, in the Korean Intellectual Property Office, the disclosure of which is incorporated herein in its entirety by reference.

BACKGROUND

1. Field

One or more exemplary embodiments relate to an ultrasound diagnosis apparatus and method, and more particularly, to an ultrasound diagnosis apparatus and method that are capable of performing texture mapping by selecting a texture corresponding to an object in a three-dimensional (3D) ultrasound volume image.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

SUMMARY

One or more exemplary embodiments include an ultrasound diagnosis apparatus and method that are capable of performing texture mapping by selecting a texture corresponding to an object in a three-dimensional (3D) ultrasound volume image.

Additional aspects will be set forth in part in the description which follows and, in part, will be apparent from the description, or may be learned by practice of the presented exemplary embodiments.

According to one or more exemplary embodiments, an ultrasound diagnosis apparatus includes: a controller configured to recognize an object included in an ultrasound image and search at least one piece of texture information corresponding to the recognized object; a display configured to display the ultrasound image and the searched at least one piece of texture information; a user interface configured to receive an input for selecting one piece of texture information from among the searched at least one piece of texture information; and an image processor configured to perform texture mapping of the selected piece of texture information onto at least one region in the ultrasound image of the object.

The controller may recognize the object based on an input for selecting the object included in the ultrasound image from among a plurality of objects.

The controller may recognize the object by comparing the ultrasound image of the object with at least one reference image.

The controller may recognize the object based on environment setting information of the ultrasound diagnosis apparatus.

The environment setting information of the ultrasound diagnosis apparatus may include a type of application and a type of a probe used for acquiring the ultrasound image of the object.

The user interface may receive an input for setting at least one region of interest (ROI) in the ultrasound image of the object and an input for selecting texture information for each of the at least one ROI from among the searched at least one piece of texture information, and the image processor may perform texture mapping of the selected texture information onto each of the at least one ROI.

The texture information may include at least one selected from the group consisting of color information, transparency, and a normal map.

The at least one piece of texture information may be obtained from an external image.

The at least one piece of texture information may be obtained based on an input for setting the texture information.

The ultrasound diagnosis apparatus may further include a memory configured to store the texture information.

If new texture information is added, or the stored at least one piece of texture information is edited or deleted, the controller may update the at least one piece of texture information by reflecting the addition, editing or deletion, and the memory may store the updated at least one piece of texture information.

The image processor may reflect at least one selected from the group consisting of effects of an external light source, reflected light, and shade on the object, thereby performing texture mapping of selected piece of texture information onto the at least one region in the ultrasound image of the object.

The image processor may perform texture mapping of the selected piece of texture information onto the at least one region in the ultrasound image of the object, based on surface rendering or volume rendering.

The ultrasound diagnosis apparatus may further include a probe configured to transmit an ultrasound signal to the object and receive an echo signal reflected from the object.

According to one or more exemplary embodiments, an ultrasound diagnosis method includes: recognizing an object included in an ultrasound image; searching at least one piece of texture information corresponding to the recognized object; displaying the ultrasound image and the searched at least one piece of texture information; receiving an input for selecting one piece of texture information from among the searched at least one piece of texture information; and performing texture mapping of the selected piece of texture information onto at least one region in the ultrasound image of the object.

The object may be recognized based on an input for selecting the object included in the ultrasound image from among a plurality of objects.

The object may be recognized by comparing the ultrasound image of the object with at least one reference image.

The object may be recognized based on environment setting information of an ultrasound diagnosis apparatus.

The environment setting information of an ultrasound diagnosis apparatus may include a type of application and a type of a probe used for acquiring the ultrasound image of the object.

According to one or more exemplary embodiments, a non-transitory computer-readable recording medium has recorded thereon a program for executing the ultrasound diagnosis method according to the one or more exemplary embodiments on a computer.

BRIEF DESCRIPTION OF THE DRAWINGS

These and/or other aspects will become apparent and more readily appreciated from the following description of the exemplary embodiments, taken in conjunction with the accompanying drawings in which:

FIG. 4 is a block diagram of an ultrasound diagnosis apparatus according to another exemplary embodiment;

FIGS. 6A and 6B are other diagrams for explaining an operation of performing texture mapping onto an ultrasound image;

FIG. 9 is a flowchart of an ultrasound diagnosis method according to an exemplary embodiment.

DETAILED DESCRIPTION

Figure 1:
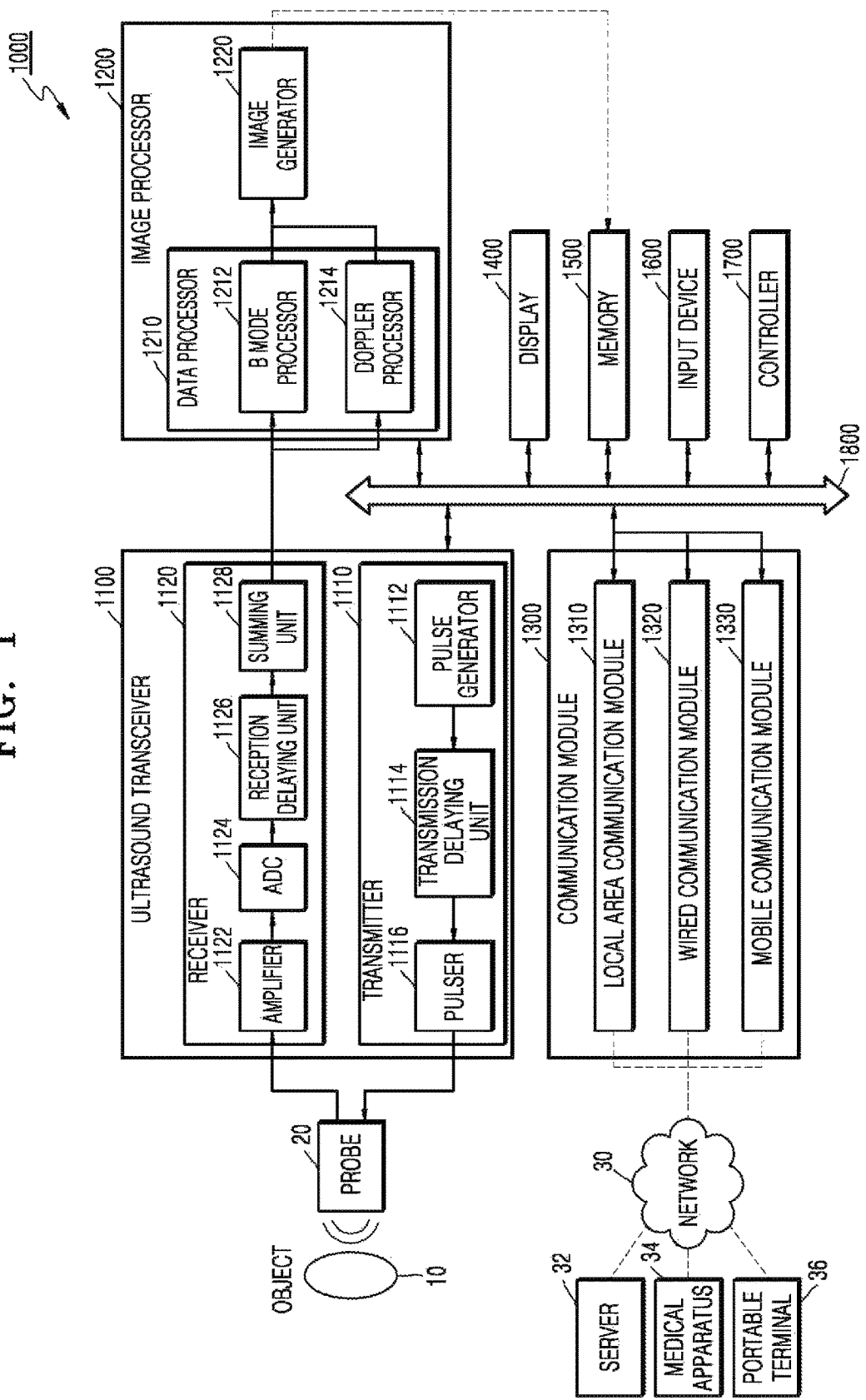
FIG. 1 is a block diagram of a configuration of an ultrasound diagnosis apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. Expressions such as "at least one of," when preceding a list of elements, modify the entire list of elements and do not modify the individual elements of the list.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Embodiments of the invention now will be described more fully hereinafter with reference to the accompanying drawings, in which illustrative embodiments of the invention are shown.

FIG. 1 is a block diagram of a configuration of an ultrasound diagnosis apparatus 1000 according to an embodiment. Referring to FIG. 1, the ultrasound diagnosis apparatus 1000 may include a probe 20, an ultrasound transceiver 1100, an image processor 1200, a communication module 1300, a display 1400, a memory 1500, an input device 1600, and a controller 1700, which may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly.

A transmitter 1110 supplies a driving signal to the probe 20. The transmitter 1110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1166. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 30 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 30 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 1700 may control all operations of the ultrasound diagnosis apparatus 1000. In other words, the controller 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the controller 1700 may be implemented as software modules. Furthermore, at least one selected from the ultrasound transceiver 1100, the image processor 1200, and the communication module 1300 may be included in the controller 1600. However, embodiments are not limited thereto.

Figure 2:
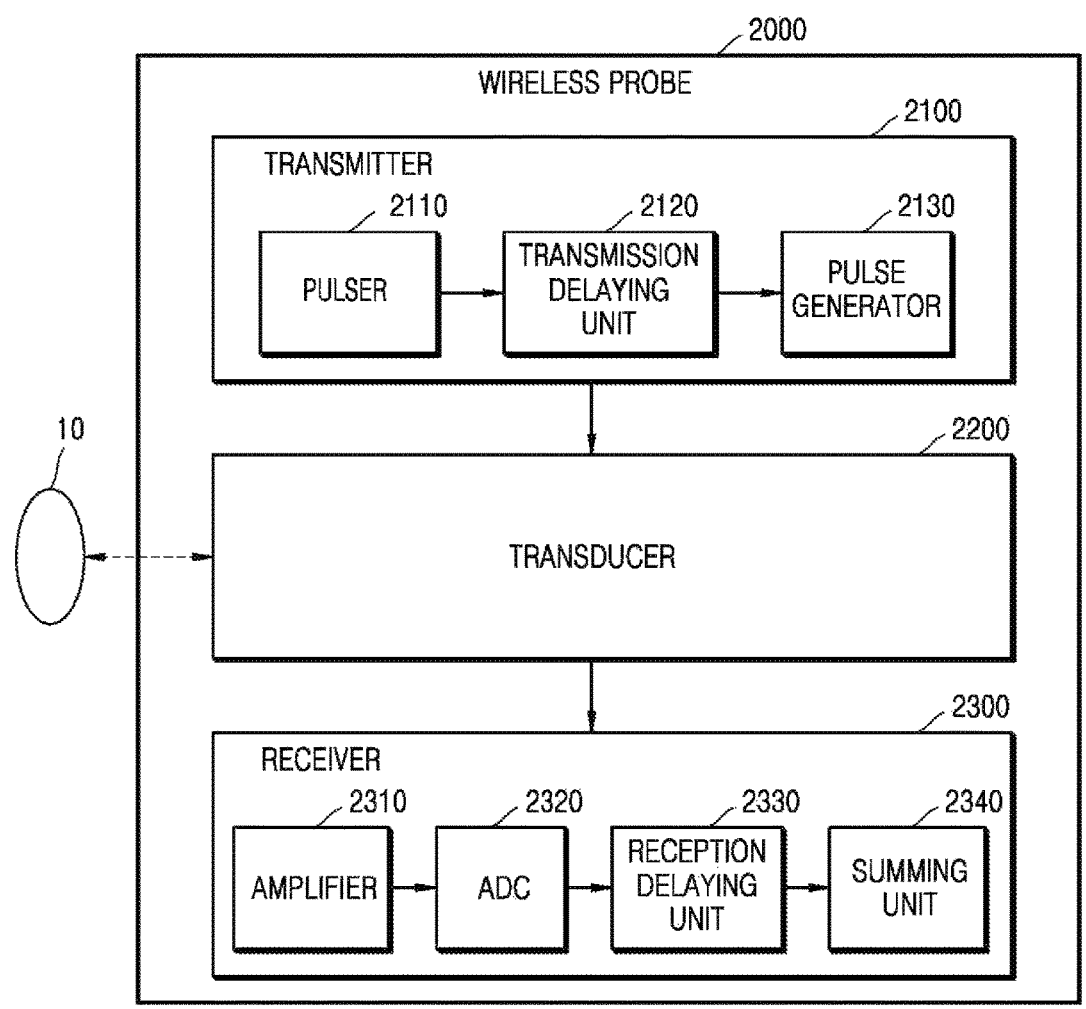
FIG. 2 is a block diagram of a configuration of a wireless probe according to an exemplary embodiment.

FIG. 2 is a block diagram of a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

In general, a user utilizes an image processing technique such as a pseudo color method in order to efficiently analyze an ultrasound image. However, despite using a technique such as a pseudo color method, users other than experienced medical practitioners have difficulty in analyzing ultrasound images. Thus, there remains a need for an ultrasound diagnosis apparatus that can provide more intuitive ultrasound images.

Ultrasound diagnosis apparatuses and methods according to one or more exemplary embodiments that are capable of providing a "texture-mapped" ultrasound image will now be described in more detail with reference to the figures.

Throughout the specification, "texture mapping" is an image processing technique for adding texture information including color information, transparency, and a normal map to an ultrasound image of an object. An ultrasound diagnosis apparatus uses texture mapping to generate a realistic ultrasound image, thereby allowing a user to intuitively analyze the ultrasound image.

Figure 3:
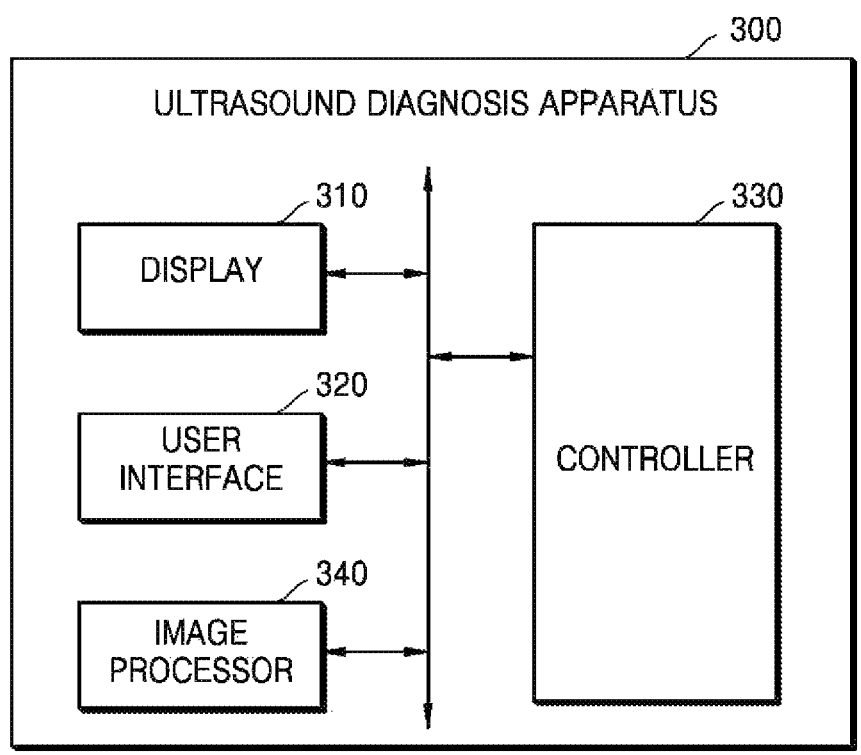
FIG. 3 is a block diagram of an ultrasound imaging apparatus according to another exemplary embodiment.

FIG. 3 is a diagram illustrating an ultrasound imaging apparatus 300 according to another exemplary embodiment.

The ultrasound diagnosis apparatus 300 according to the present embodiment may include a display 310, a user interface 320, a controller 330, and an image processor 340.

The ultrasound diagnosis apparatus 300 may be another embodiment of the ultrasound diagnosis apparatus 100 of FIG. 1. In detail, the display 310, the user interface 320, the controller 330, and the image processor 340 of FIG. 3 may respectively correspond to or include the display 1400, the input device 1600, the controller 1700, and the image processor 1200. Thus, the same descriptions as already presented with respect to FIG. 1 are omitted.

The controller 330 may control overall operations of the ultrasound diagnosis apparatus 300. In detail, the controller 330 may control operations of the display 310, the user interface 320, and the image processor 340.

The controller 330 recognizes an object in an ultrasound image and searches at least one piece of texture information corresponding to the recognized object.

In this case, 'recognizing an object in an ultrasound image" means identifying which part of a body is an object in an ultrasound image. For example, the controller 330 may identify the object in the ultrasound image as being the heart, colon, or liver according to various methods that will be described below.

The controller 330 may manually recognize the object based on a user input. Alternatively, the controller 330 may automatically recognize the object by comparing an ultrasound image of the object with a reference image or based on environment setting information of the ultrasound diagnosis apparatus 300. Methods used by the controller 330 to recognize an object will be described in more detail below with reference to FIGS. 6 and 7.

As described above, the object may include a human or an animal, or a part of a human or animal. For example, the object may be an organ (e.g., the liver, the heart, the womb, the brain, a breast, or the abdomen), a blood vessel, or a phantom. Throughout the specification, an "ultrasound image" includes a 3D ultrasound image.

The display 310 displays a predetermined user interface screen. In detail, the display 310 may display an ultrasound image and at least one piece of texture information searched by the controller 330. The user interface screen displayed by the display 310 will be described in more detail below with reference to FIGS. 5 through 8.

The display 310 may display texture information in the form of an image. In detail, the display 310 may display an image to which texture information is applied (hereinafter, referred to as a "texture image") so that a user may efficiently select the texture information to be mapped onto an ultrasound image of an object. In addition, the display 310 may display texture information based on at least one type selected from letters, numbers, and symbols.

Furthermore, "texture information" may include at least one selected from color information, transparency, and a normal map as well as a predetermined pattern consisting of at least one combination of the color information, the transparency, and the normal map.

For example, the display 310 may display texture images respectively showing the skin, blood vessel, liver, and heart. The texture images displayed by the display 310 will be described in more detail below with reference to FIGS. 5 through 8.

Texture information may be obtained from external images. In detail, the texture information may be acquired from external images including ultrasound, CT, X-ray, MRI, and endoscopic images as well as photo or picture files. For example, in one or more exemplary embodiments, the ultrasound diagnosis apparatus 300 may obtain texture information of an inner wall of an organ from an endoscopic image.

Texture information may also be obtained by a combination of external images. For example, color information contained in the texture information may be acquired from a first external image, and a normal map contained therein may be acquired from a second external image.

Texture information may also be obtained based on an input for setting the texture information. In detail, a user may directly set at least one selected from color information, transparency, and a normal map contained in the texture information. Furthermore, the user may directly set a predetermined pattern of the texture information consisting of at least one combination of color information, transparency, and normal map. For example, in order to set texture information of a skin, the user may set color information of the skin and a normal map for representing irregularities on the skin.

The user interface 320 may receive an input for selecting one piece of texture information from among at least one piece of the texture information that is displayed by the display 310 or searched by the controller 330. The selected piece of texture information corresponds to information that is texture-mapped onto at least one region in an ultrasound image of an object.

Even a texture of the same object in the same patient may vary depending on a patient's health condition or constitution. Textures of the same object in different patients may also vary for the different patients. For example, textures of livers of young patients in their twenties and thirties may be different from those of livers of elderly patients in their sixties and seventies. Thus, a user may select texture information that is considered as being the most suitable for a patient's health condition or constitution from among at least one piece of texture information displayed by the display 310.

For example, in order to map texture information of a fetal skin onto a fetal ultrasound image contained in an ultrasound image, a user may select a texture image showing the fetal skin from among texture information displayed by the display 310. The user interface 320 may also receive a user input for selecting the texture image showing the fetal skin and transmit the received user input to the controller 330.

In detail, the user interface 320 generates and outputs a user interface screen for receiving a predetermined command or data from a user and receives the predetermined command or data from the user via the user interface screen. The user interface screen output from the user interface 320 is also output to the display 310 that may in turn display the user interface screen. The user may then view the user interface screen displayed via the display 310 to recognize predetermined information and input a predetermined command or data The user interface 320 may include a mouse, a keyboard, or another input device including hard keys for receiving predetermined data. For example, the user may enter predetermined data or command by manipulating at least one selected from the mouse, the keyboard, and the other input device in the user interface 320.

In another example, the user interface 320 may be formed as a touch pad. In detail, the user interface 320 includes a touch pad (not shown) combined with a display panel (not shown) in the display 310 and outputs a user interface screen to the display panel. When a predetermined command is input via the user interface screen, the touch pad may detect the input of the predetermined command, thereby recognizing the predetermined command input by a user.

In detail, if the user interface 320 is formed as a touch pad, when the user touches a predetermined point on the user interface screen, the user interface 320 detects a touched point. The user interface 320 may then transmit information about the detected touched point to the controller 330. The controller 330 may then recognize a user request or command corresponding to a menu displayed at the detected point and perform image processing on an ultrasound image according to the recognized user request or command.

The image processor 340 performs texture mapping of selected texture information onto at least one region in an ultrasound image of an object. In this case, the at least one region in the ultrasound image of the object may be set by a user or via operations in a predetermined algorithm performed by the controller 330. The at least one region may be the whole object or a region of the object.

The display 310 may also display an ultrasound image of an object that has undergone texture mapping performed by the image processor 340, thereby allowing a user to efficiently and intuitively analyze the object.

FIG. 4 is a block diagram of an ultrasound diagnosis apparatus 400 according to another exemplary embodiment.

The ultrasound diagnosis apparatus 400 according to the present embodiment may further include a probe 450 and a memory 460 in comparison to the ultrasound diagnosis apparatus 300 of FIG. 3. The other components correspond to their counterparts in the ultrasound diagnosis apparatus 300 of FIG. 3. In detail, a display 410, a user interface 420, a controller 430, and an image processor 440 respectively correspond to the display 310, the user interface 320, the controller 330, and the image processor 340 in the ultrasound diagnosis apparatus 300. Thus, the same descriptions as already presented with respect to FIG. 3 are omitted.

Furthermore, if the ultrasound diagnosis apparatus 400 is included in the ultrasound diagnosis apparatus 100 of FIG. 1, the probe 450 of FIG. 4 may correspond to or be included in the probe 20 of FIG. 1. Similarly, the memory 460 of FIG. 4 may correspond or be included in the memory 1500 of FIG. 1. Thus, the same descriptions as already presented with respect to FIG. 1 are omitted.

The memory 460 may store at least one piece of texture information.

If new texture information is added, or texture information stored in the memory 460 is edited or deleted, the controller 430 may update at least one piece of texture information by reflecting such addition, editing or deletion. The memory 460 may store the at least one piece of texture information updated by the controller 430.

In detail, the controller 430 may update texture information stored in the memory 460 based on a user input. Alternatively, the controller 430 may update texture information stored in the memory 460 according to the latest texture information received from the communication module 1300.

For example, the controller 430 may edit 24-bit RGB color information contained in texture information, add or delete a point, a line, a face, and a polygon, or adjust brightness, contrast, saturation, hue, transparency, etc. of the texture information. As another example, the controller 430 may update texture information by rotating or symmetrically displacing a texture image.

Figure 5A:
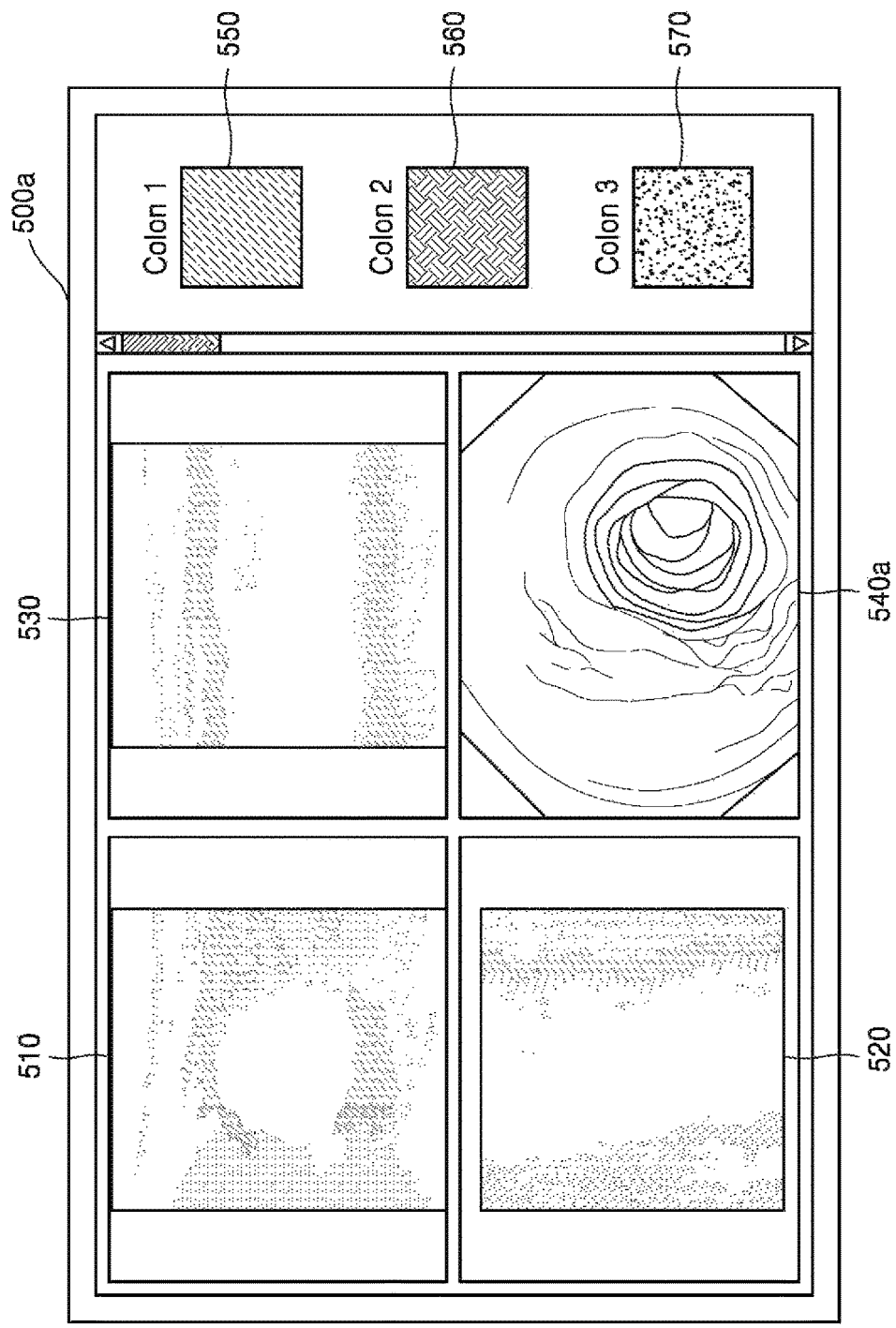
FIGS. 5A and 5B are diagrams for explaining an operation of performing texture mapping onto an ultrasound image according to an exemplary embodiment.
Figure 5B:
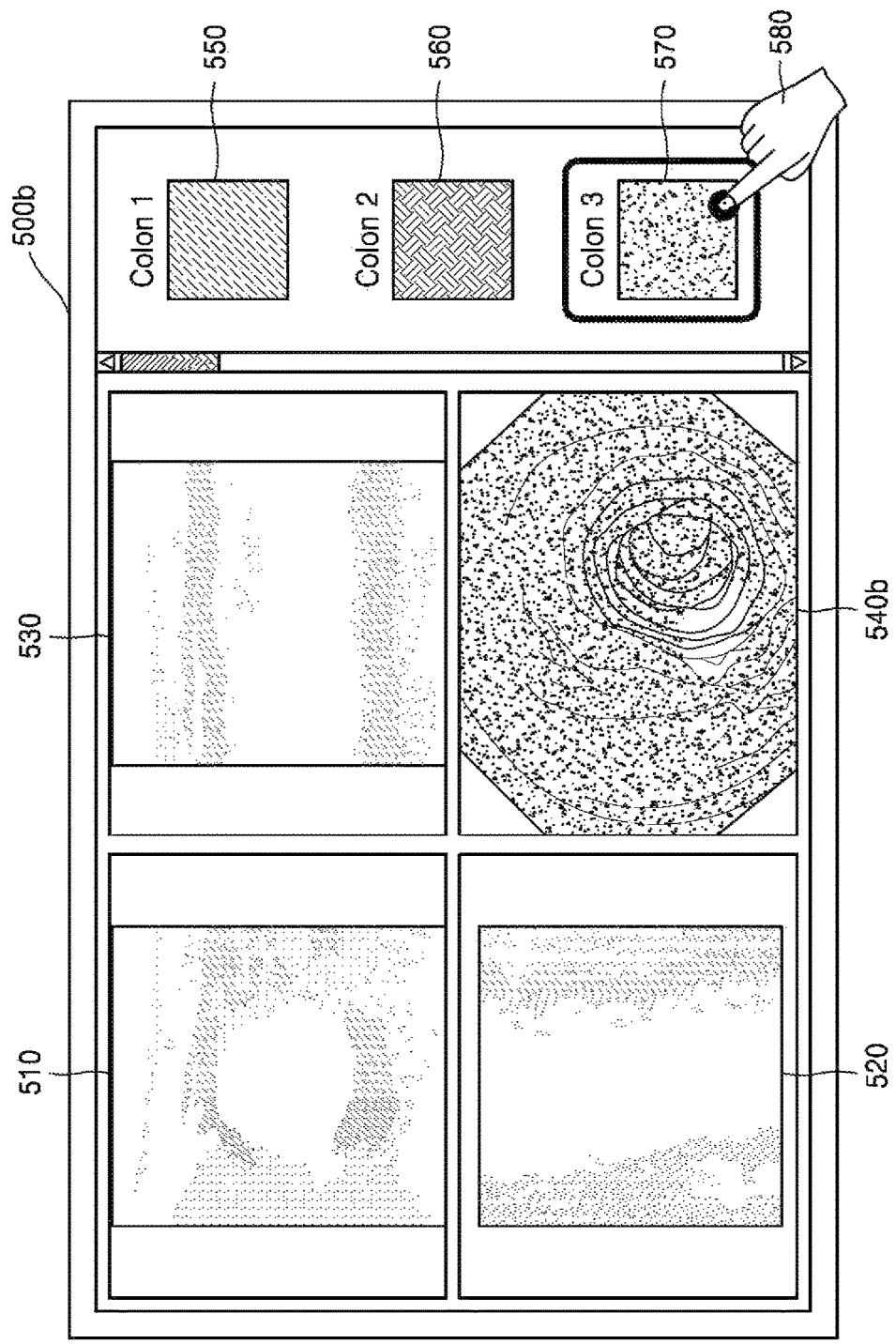

FIGS. 5A and 5B are diagrams for explaining an operation of performing texture mapping onto an ultrasound image according to an exemplary embodiment. In detail, FIGS. 5A and 5B are diagrams for explaining operation of the ultrasound diagnosis apparatus 300 (400) performing texture mapping on 3D ultrasound images 540*a* and 540*b* of a colon. The 3D ultrasound images 540*a* and 540*b* of the inside of the colon may be acquired using functions of the ultrasound diagnosis apparatus 300 (400) such as an endoscopic view function.

FIGS. 5A and 5B illustrate user interface screens 500*a* and 500*b* that are respectively displayed on the display 310 (410) before and after the image processor 340 (440) of the ultrasound diagnosis apparatus 300 (400) performs texture mapping onto the 3D ultrasound images 540*a* and 540*b*.

Referring to FIG. 5A, the display 310 (410) may display predetermined cross-sectional images 510, 520, and 530 for the 3D ultrasound image 540*a* of the colon. Orientations and positions of cross-sections in the predetermined cross-sectional images 510, 520, and 530 may be set based on user settings.

The display 310 (410) may also display at least one texture image searched by the controller 330 (430). For example, the display 310 (410) may display first through third colon texture images 550, 560, and 570.

Furthermore, the first through third colon texture images 550, 560, and 570 may be obtained from at least one selected from an ultrasound image, a CT image, an X-ray image, an MRI image, an endoscopic image, a photo, and a picture, or based on a user input. For example, the first and third colon texture images 550 and 570 may be acquired from an endoscopic image and a photo of the colon, respectively, and the second colon texture image 560 may be acquired based on a user input.

Referring to FIG. 5B, the user interface 320 (420) may receive an input 580 for selecting the third colon texture image 570. The image processor 340 (440) may then perform texture mapping of texture information of the selected third colon texture image 570 onto at least one region in the 3D ultrasound image 540b of the colon.

In detail, the image processor 340 (440) may add color information, transparency, and a normal map in the texture information to the at least one region in the 3D ultrasound image 540b of the colon. The 3D ultrasound image 540b of the colon that has undergone the texture mapping may show the colon in a realistic way. Furthermore, a user is able to intuitively identify a patient's health condition by viewing the 3D ultrasound image 540b of the colon.

The image processor 340 (440) may reflect at least one selected from effects of an external light source, reflected light, and shade on an object, thereby performing texture mapping of selected texture information onto at least one region in an ultrasound image of the object.

In detail, the image processor 340 (440) may perform image processing on an ultrasound image in such a manner as to achieve the same effect as when an external light source emits light toward the object. A position of the external light source and a direction and intensity of light emitted from the external light source may be set based on a user input.

Furthermore, the image processor 340 (440) may perform image processing on an ultrasound image of the object so as to generate reflected light when light emitted from the external light source reflects off the object. Reflectance of the object may be set based on a user input.

The image processor 340 (440) may perform texture mapping of selected information onto at least one region in an ultrasound image of an object based on surface rendering or volume rendering.

If texture mapping is performed based on surface rendering, the image processor 340 (440) may set a plurality of meshes on a surface of an ultrasound image of an object and perform the texture mapping for each of the plurality of meshes.

Otherwise, if texture mapping is performed based on volume rendering, the image processor 340 (440) may perform the texture mapping of texture information for voxels on a surface of an ultrasound image of an object as well as all other voxels in the ultrasound image of the object.

Texture mapping based on surface rendering requires less computation and accordingly takes less time to compute than texture mapping based on volume rendering. On the other hand, the texture mapping based on volume rendering allows reconstruction of a more realistic ultrasound image than the texture mapping based on surface rendering.

Figure 6A:
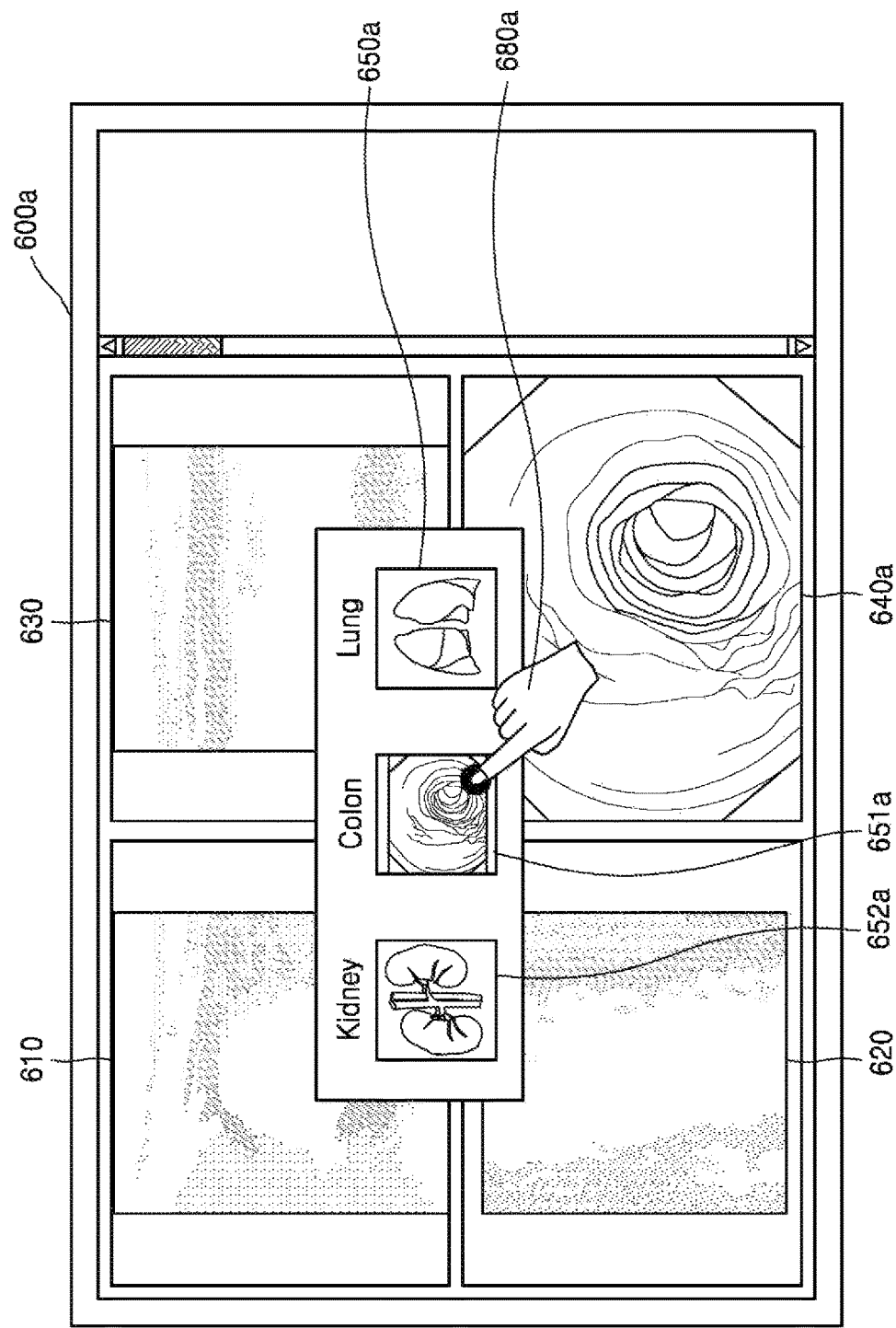

FIGS. 6A and 6B are diagrams for explaining an operation of performing texture mapping onto an ultrasound image according to another exemplary embodiment. In detail, FIGS. 6A and 6B are other diagrams for explaining an operation of the ultrasound diagnosis apparatus 300 (400) for performing texture mapping onto 3D ultrasound images 640a and 640b of a colon.

Since user interface screens 600a and 600b of FIGS. 6A and 6B incorporate the same technical concepts as the user interface screens 500a and 500b, the same descriptions as already presented with respect to FIGS. 5A and 5B are omitted.

FIGS. 6A and 6B illustrate the user interface screens 600a and 600b that are respectively displayed on the display 310 (410) before and after the image processor 340 (440) of the ultrasound diagnosis apparatus 300 (400) performs texture mapping onto the 3D ultrasound images 640a and 640b.

The display 310 (410) may display predetermined cross-sectional images 610, 620, and 630 for the 3D ultrasound image 640a of the colon. Orientations and positions of cross-sections in the predetermined cross-sectional images 610, 620, and 630 may be set based on user settings.

In one or more exemplary embodiments, the ultrasound diagnosis apparatus 300 (400) may search at least one piece of texture information corresponding to an object in an ultrasound image.

In detail, the controller 330 (430) may recognize an object included in an ultrasound image based on an input for selecting the object from among a plurality of objects.

For example, according to control by the controller 330 (430), the display 310 (410) may display a plurality of objects respectively corresponding to at least one piece of texture information. The user interface 320 (420) may then receive an input for selecting an object corresponding to an ultrasound image from among the plurality of objects displayed by the display 310 (410).

The controller 330 (430) may also search at least one piece of texture information corresponding to the recognized object.

For example, the controller 330 (430) may recognize an object and search at least one piece of texture information corresponding to the recognized object from among at least one piece of texture information stored in the memory 460.

Referring to FIG. 6A, the display 310 (410) may display a plurality of objects, i.e., a kidney 650a, a colon 651a, and a lung 652a respectively corresponding to at least one piece of texture information. The user interface 320 (420) may receive an input 680a for selecting the colon 651a from among the plurality of objects, i.e., the kidney 650a, the colon 651a, and the lung 652a. The selected colon 651a corresponds to a colon in the 3D ultrasound image 640a, and the controller 330 (430) may recognize the object included in the ultrasound image as the colon.

The controller 330 (430) may also search at least one texture information corresponding to the colon, and the display 310 (410) may display the at least one piece of texture information searched by the controller 330 (430). The user interface 320 (420) may receive an input for selecting one from among the at least one piece of information displayed by the display 310 (410). The image processor 340 (440) may perform texture mapping of the selected texture information onto the ultrasound image of the object.

For example, referring to FIG. 6B, the display 310 (410) may display at least one texture image corresponding to the colon 651a, i.e., first through third colon texture images 660b, 661b, and 662b searched by the controller 330 (430). The user interface 320 (420) may receive an input 680b for selecting the second colon texture image 661b from among the first through third colon texture images 660b, 661b, and 662b. In detail, a user may select texture information that is the most suitable for a patient's health condition or constitution. The image processor 340 (44) may perform texture mapping of the second colon texture image 661b onto the 3D ultrasound image 640b of a colon.

Furthermore, according to one or more exemplary embodiments, the ultrasound diagnosis apparatus 300 (400) may change texture information that is texture-mapped onto an ultrasound image of an object based on an input.

In detail, the user interface 320 (420) may receive an input for changing texture information that is texture-mapped onto an ultrasound image of an object to another texture information. Furthermore, the image processor 340 (440) may perform texture mapping of the other information onto at least one region in the ultrasound image of the object based on the input received from the user interface 320 (420).

Figure 7A:
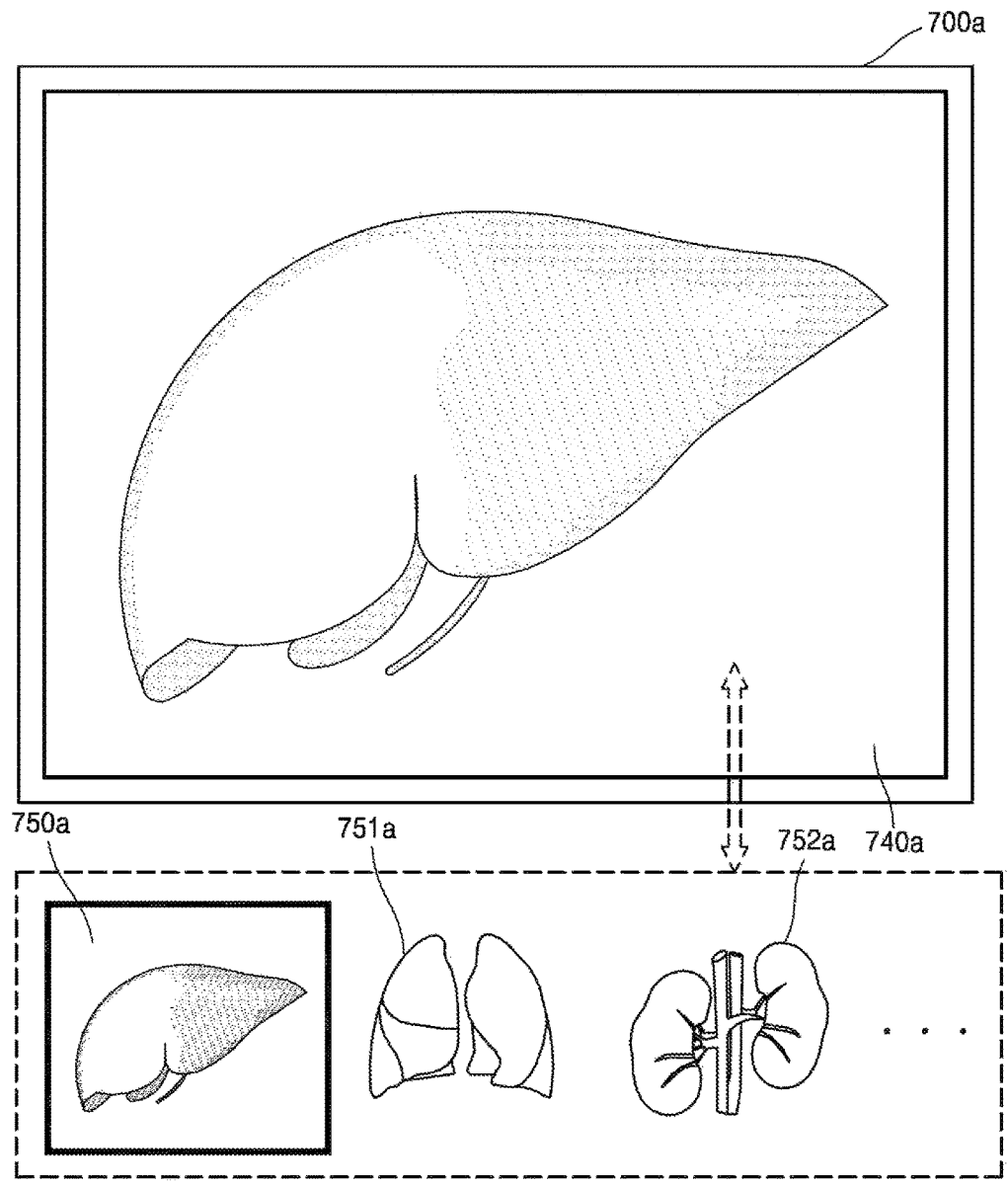
FIGS. 7A through 7C are other diagrams for explaining an operation of performing texture mapping onto an ultrasound image.
Figure 7B:
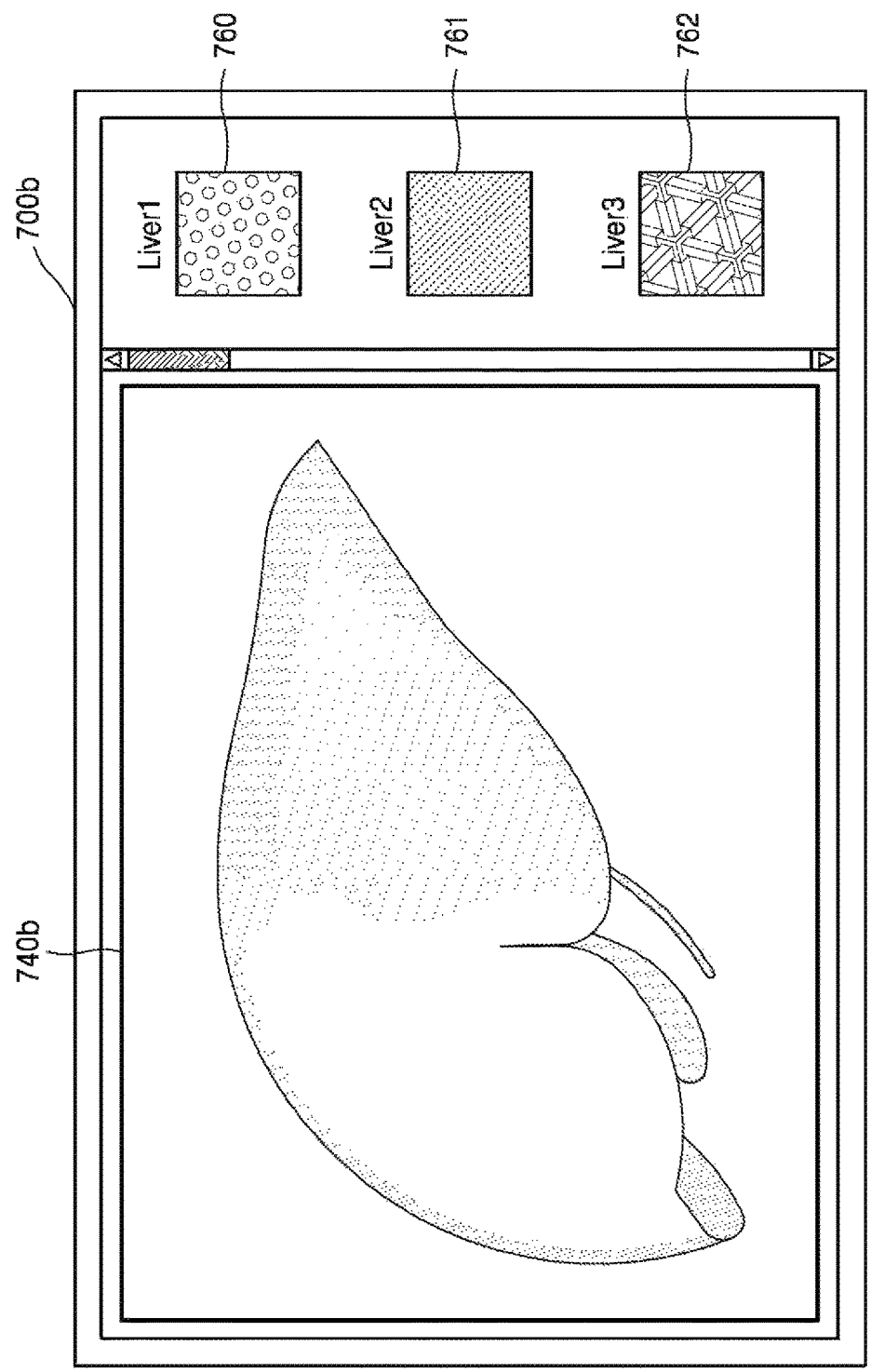
Figure 7C:
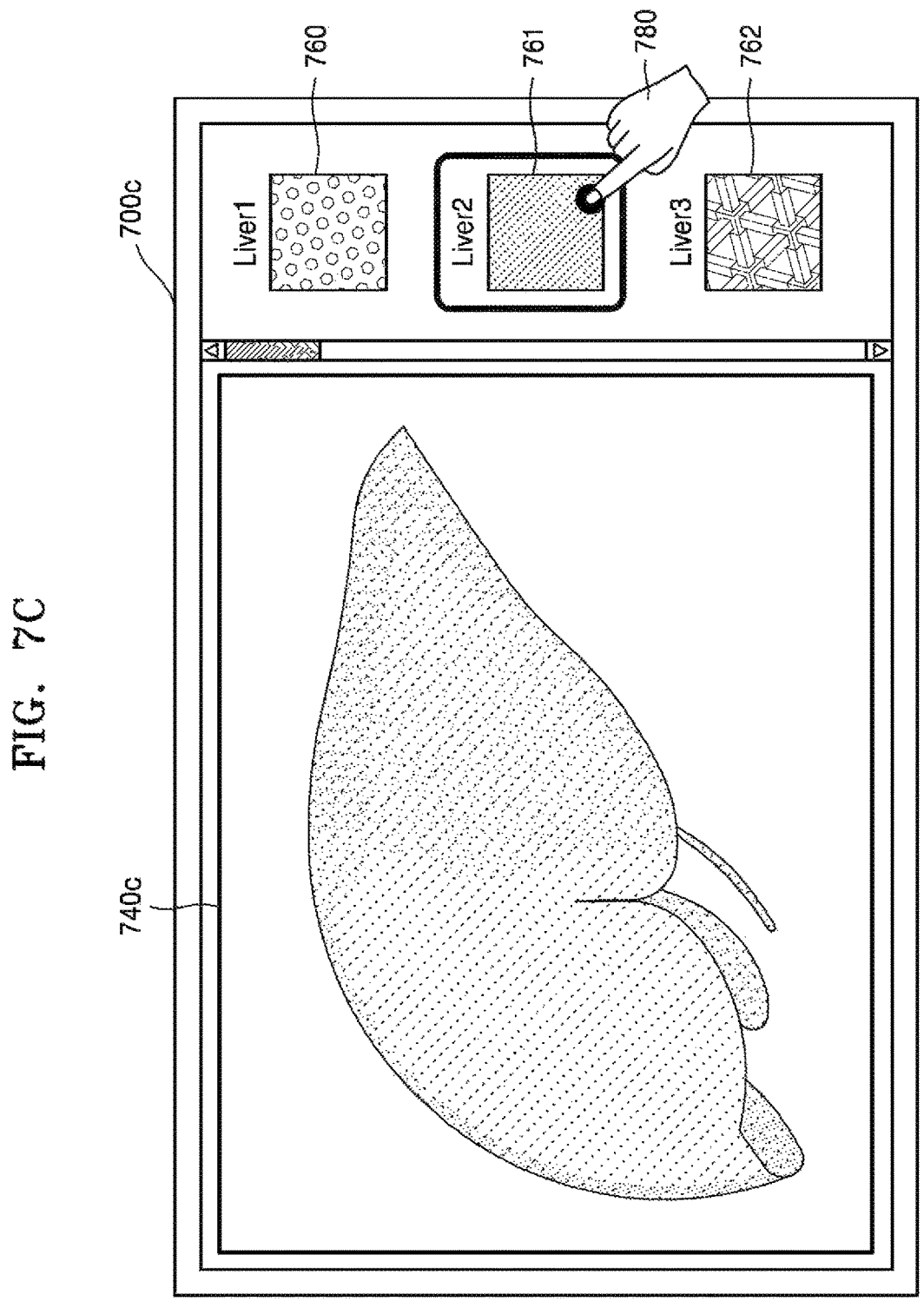

FIGS. 7A through 7C are diagrams for explaining an operation of performing texture mapping onto an ultrasound image according to another exemplary embodiment. In detail, FIGS. 7A through 7C are other diagrams for explaining an operation of the ultrasound diagnosis apparatus 300 (400) for performing texture mapping onto 3D ultrasound images 740a, 740b, and 740c of a liver.

Since user interface screens 700a through 700c of FIGS. 7A through 7C incorporate the same technical concepts as the user interface screens 500a and 500b, the same descriptions as already presented with respect to FIGS. 5A and 5B are omitted.

FIGS. 7A and 7B illustrate the user interface screens 700a and 700b that are displayed on the display 310 (410) before the image processor 340 (440) of the ultrasound diagnosis apparatus 300 (400) performs texture mapping onto the 3D ultrasound images 740a and 740b. FIG. 7C illustrates the user interface screen 700c that is displayed on the display 310 (410) after the image processor 340 (440) performs texture mapping onto the 3D ultrasound image 740c.

Another approach to recognizing an object includes the controller 330 (430) comparing an object in an ultrasound image with at least one reference image. In this case, a "reference image" means a general ultrasound image showing the outside or inside of an object such as the heart, liver, or colon. The memory 460 may store at least one reference image.

For example, the controller 330 (430) may compare an ultrasound image of an object displayed by the display 310 (410) with at least one reference image stored in the memory 460, select a first reference image that is most similar to the ultrasound image of the object, and search at least one piece of texture information corresponding to the first reference image.

Referring to FIG. 7A, the memory 460 stores reference images 750a, 751a, and 752a of a liver, a lung, and a kidney. The controller 330 (430) may compare the 3D ultrasound image 740a displayed by the display 310 (410) with at least one of the reference images 750a, 751a, and 752a stored in the memory 460 and recognize an object as a liver based on the reference image 750a that is most similar to the 3D ultrasound image 740a.

Referring to FIG. 7B, the controller 330 (430) may search first through third liver texture images 760 through 762 corresponding to the object recognized as the liver. Furthermore, the display 310 (410) may display the searched first through third liver texture images 760 through 762 according to control by the controller 330 (430).

Referring to FIG. 7C, the user interface 320 (420) may receive an input for selecting the second liver texture image 761 from among the first through third liver texture images 760 through 762 displayed by the display 310 (410). The user may select texture information that is most suitable for a patient's health condition or constitution. The image processor 340 (440) may perform texture mapping of the selected second liver texture image 761 onto at least one region in the 3D ultrasound image 740c.

Another approach to recognizing an object is to recognize the object based on environment setting information of the ultrasound diagnosis apparatus 300 (400). The environment setting information may be information necessary for directly or indirectly recognizing the object. For example, types of an application and a probe used for acquiring an ultrasound image of an object may be information for identifying the object.

In detail, a convex array probe that can acquire an ultrasound image of a relatively wide area may be used to examine organs in the abdomen. A linear array probe may be used for examinations of breasts, thyroid gland, musculoskeletal system, or other structures. A phased array probe may be used to image the heart via a space between ribs.

As described above, since the type of an object to be examined may vary according to the type of a probe, the type of a probe may be information necessary for recognizing the object. Thus, the controller 330 (430) may recognize an object based on the type of a probe used for acquiring an ultrasound image of the object. For example, if a phased array probe is used, the controller 330 (430) may recognize an object as the heart and search texture information corresponding to the heart.

Like the type of a probe, the type of an application may be used for identifying an object. In detail, according to properties of the object, the ultrasound diagnosis apparatus 300 (400) may perform a different image processing method or provide different functions to the user. Thus, based on the type of application used for acquiring an ultrasound image, the controller 330 (430) may recognize an object and search texture information corresponding to the recognized object.

Another approach for recognizing an object is to use a predetermined algorithm. In detail, the controller 330 (430) may identify an object in an ultrasound image displayed by the display 310 (410) based on at least one of predetermined algorithms. The predetermined algorithms may include Sobel Operator, Morphological Operators (Erosion Operator, Dilation Operator, Opening Operator, Closing Operator), A*boundary-forming algorithm, F*boundary-forming algorithm, Deformable Model, Snake Algorithm, Level Set, Thresholding (Local, Adaptive, Hysteresis), Histogram Equalization (CLAHE, Retinex), k-Nearest-Neighbor (kNN) Classifier, Maximum Likelihood (ML) Classifier, Bayes Classifier, K-means clustering, fuzzy clustering, Markov Random Fields (MRF), Region Growing Algorithm, Split and Merge Algorithm, Atlas-warping Algorithm, Artificial Neural Networks (ANN), Locally Excitatory Globally Inhibitory Oscillator Network (LEGION) Algorithm, Scale Invariant Feature Transform (SIFT), Histogram of Oriented Gradient (HOG), Haar feature, Ferns, Local Binary Pattern (LBP), Modified Census Transform (MCP), and Thinning Algorithm.

Figure 8A:
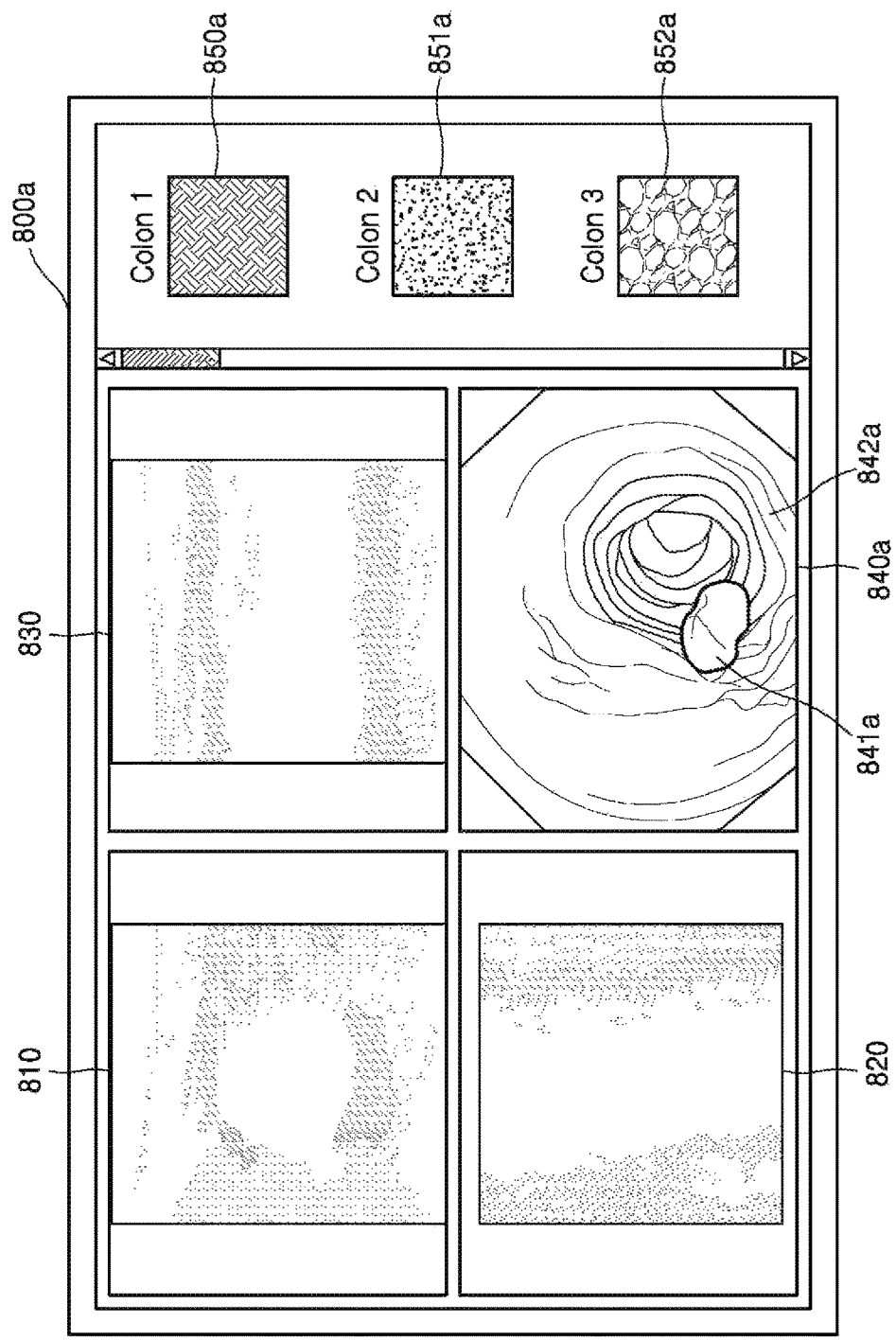
FIGS. 8A through 8C are other diagrams for explaining an operation of performing texture mapping onto an ultrasound image.
Figure 8B:
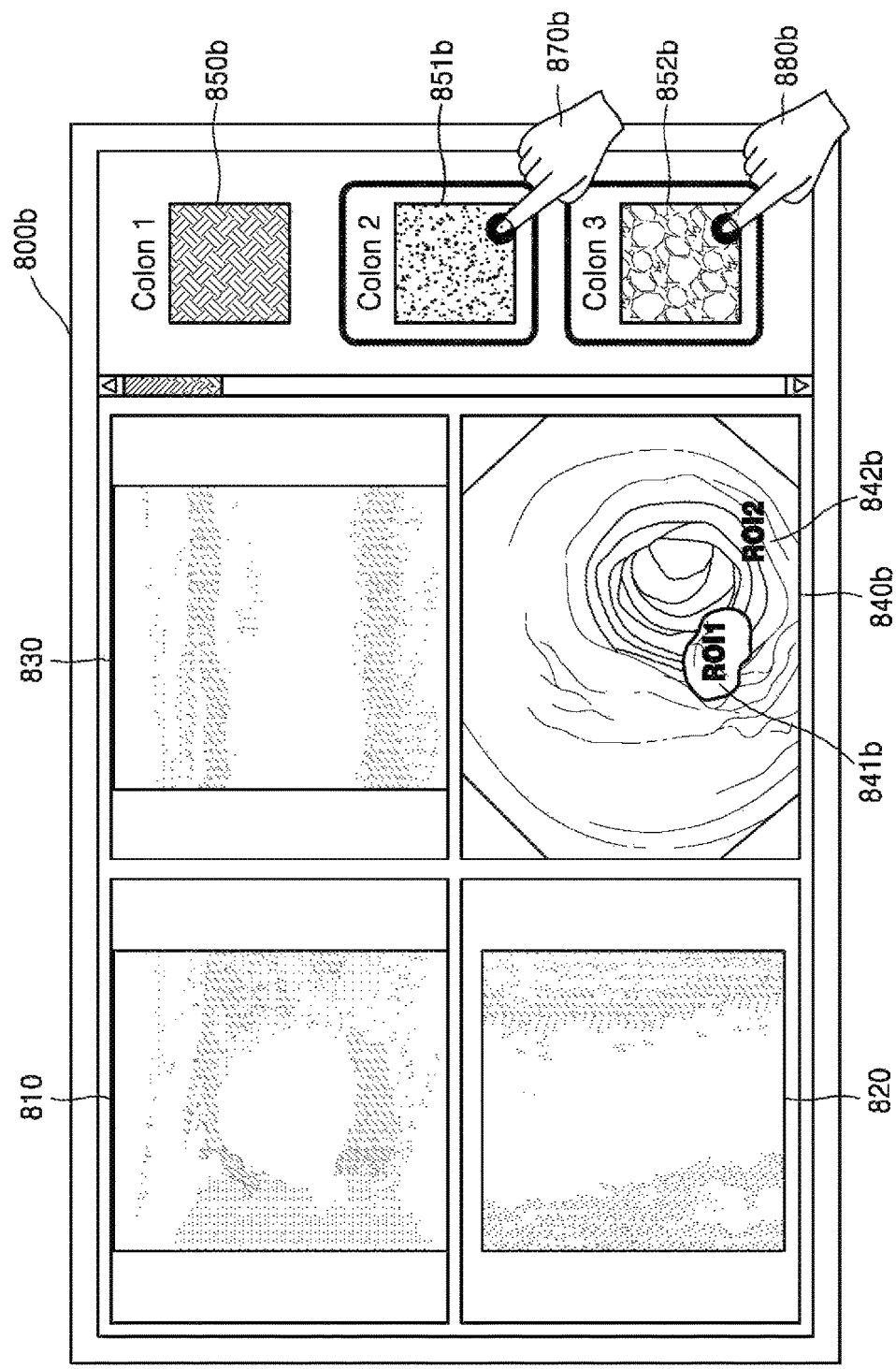
Figure 8C:
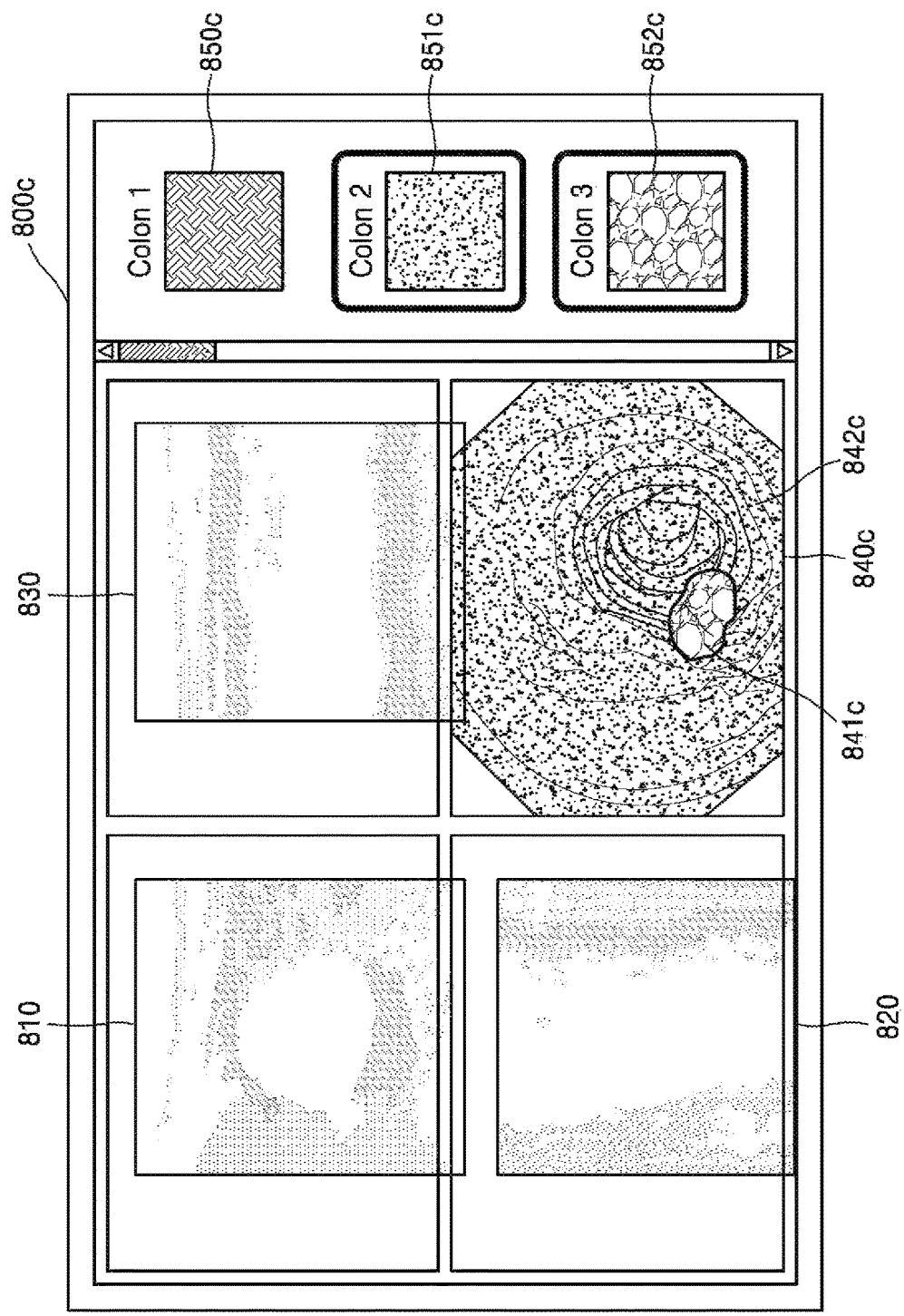

FIGS. 8A through 8C are diagrams for explaining an operation of performing texture mapping onto an ultrasound image according to another exemplary embodiment. In detail, FIGS. 8A through 8C are other diagrams for explaining an operation of the ultrasound diagnosis apparatus 300 (400) for performing texture mapping onto regions of interest (ROI) that are set in 3D ultrasound images 840a, 840b, and 840c of a colon.

Since user interface screens 800a through 800c of FIGS. 8A through 8C incorporate the same technical concepts as the user interface screens 500a and 500b, the same descriptions as already presented with respect to FIGS. 5A and 5B are omitted.

FIG. 8A illustrates the user interface screen 800a that is displayed on the display 310 (410) before the image processor 340 (440) of the ultrasound diagnosis apparatus 300 (400) performs texture mapping onto the 3D ultrasound image 840a. FIG. 8B illustrates the user interface screen 800b including the 3D ultrasound image 840b where an ROI is set. FIG. 8C illustrates the user interface screen 800c that is displayed on the display 310 (410) after the image processor 340 (440) performs texture mapping onto the 3D ultrasound image 840c.

The display 310 (410) may display predetermined cross-sectional images 810, 820, and 830 for an ultrasound image of an object. Orientations and positions of cross-sections in the predetermined cross-sectional images 810, 820, and 830 may be set based on user settings.

According to one or more exemplary embodiments, the ultrasound diagnosis apparatus 300 (400) may set at least one ROI in the ultrasound image of the object and perform texture mapping for each ROI.

If an ultrasound image includes a plurality of objects, different pieces of texture information needs to be mapped for each object. Alternatively, if an ultrasound image includes a single object, different pieces of texture information may be mapped for each of regions into which the object is segmented. For example, if a cancer cell is found in an ultrasound image of a liver, the ultrasound diagnosis apparatus 300 (400) may perform texture mapping on an ultrasound image of the liver by using different pieces of texture information for a cancer cell and a normal cell, respectively. In this case, the ultrasound diagnosis apparatus 300 (400) may provide a more useful ultrasound image to a user.

In detail, the user interface 320 (420) may receive an input for setting at least one ROI in an ultrasound image of an object and an input for selecting texture information for each of the at least one ROI from among at least one piece of texture information. Furthermore, the image processor 340 (440) may perform texture mapping of the selected texture information onto each of the at least one ROI.

For example, as shown in FIG. 8A, the 3D ultrasound image 840a may include an ultrasound image 841a of an abnormal tissue. The ultrasound diagnosis apparatus 300 (400) may perform texture mapping of different pieces of texture information on the ultrasound image 841a of the abnormal tissue and the remaining 3D ultrasound image 842a other than the abnormal tissue.

FIG. 8B illustrates an operation of the ultrasound diagnosis apparatus 300 (400) for setting an ROI in the 3D ultrasound image 840b. In detail, the user interface 320 (420) may receive an input for respectively setting an ultrasound image 841b of an abnormal tissue and the remaining 3D ultrasound image 842b as first and second ROIs. Furthermore, the user interface 320 (420) may receive an input 880b for selecting a third colon texture image 852b for the first ROI and an input 870b for selecting a second colon texture image 851b for the second ROI.

FIG. 8C illustrates the 3D ultrasound image 840c obtained by performing texture mapping of different pieces of texture information for each ROI. In detail, the image processor 340 (440) may perform texture mapping of third and second colon texture images 852c and 851c onto first and second ROIs 841c and 842c, respectively, based on the inputs 880b and 870b received from the user interface 320 (420).

FIG. 9 is a flowchart of an ultrasound diagnosis method 900 according to an exemplary embodiment. The ultrasound diagnosis method 900 may include the same operations as those performed by the ultrasound diagnosis apparatus 300 (400) described above with reference to FIGS. 1 through 8. Thus, descriptions of the ultrasound diagnosis method 900 corresponding to descriptions already presented with respect to FIGS. 1 through 8 are omitted.

Referring to FIG. 9, an object included in an ultrasound image is recognized (S910). Operation S910 may be performed by the controller 330 (430) of the ultrasound diagnosis apparatus 300 (400).

In detail, in operation S910, the object may be recognized based on an input for selecting the object in the ultrasound image. According to another exemplary embodiment, the object may be recognized by comparing the ultrasound image of the object with at least one reference image. According to another exemplary embodiment, the object may be recognized based on environment setting information of the ultrasound diagnosis apparatus 300 (400). The environment setting information may include types of an application and a probe used for acquiring an ultrasound image of the object.

According to the ultrasound diagnosis method 900, at least one piece of texture information corresponding to the object recognized in operation S910 may be searched (S920). Operation S920 may be performed by the controller 330 (430) of the ultrasound diagnosis apparatus 300 (400).

The at least one piece of texture information searched in operation S920 may be displayed (S930). Operation S930 may be performed by the display 310 (410) of the ultrasound diagnosis apparatus 300 (400).

An input for selecting one piece of texture information from among the at least one piece of texture information that is displayed in operation S930 or searched in operation S920 may be received (S940). Operation S940 may be performed by the user interface 320 (420) of the ultrasound diagnosis apparatus 300 (400).

The one piece of texture information selected in operation S940 is texture-mapped onto an ultrasound image of the object (S950). Operation S950 may be performed by the image processor 340 (440) of the ultrasound diagnosis apparatus 300 (400).

Furthermore, the ultrasound diagnosis method 900 may be performed by the server (32 of FIG. 1), the medical apparatus (34 of FIG. 1), or the portable terminal (36 of FIG. 1) that communicate with the communication module (1300 of FIG. 1) via the network (3 of FIG. 1) by wire or wirelessly.

As described above, the ultrasound diagnosis apparatuses 300 and 400 and the ultrasound diagnosis method 900 according to the exemplary embodiments may provide a texture-mapped ultrasound image. Thus, a user is able to analyze the ultrasound image more intuitively and examine a patient more efficiently for diagnosis.

The exemplary embodiments may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

While one or more embodiments have been described with reference to the figures, it will be understood by those of ordinary skill in the art that various changes in form and details may be made therein without departing from the spirit and scope of the inventive concept as defined by the following claims.

What is claimed is:

1. An ultrasound diagnosis apparatus comprising:
a controller configured to recognize an object shown in an ultrasound image based on an input for selecting the object shown in the ultrasound image from among a plurality of objects, identify a type of the recognized object from among a set of types of a set of objects, and search at least one piece of texture information corresponding to the identified type of the object from among a set of pieces of texture information corresponding to the set of objects;
a display configured to display the ultrasound image and the searched at least one piece of texture information corresponding to the identified type of the object;
a user interface configured to receive an input for selecting one piece of texture information from among the searched at least one piece of texture information; and
an image processor configured to perform texture mapping of the selected piece of texture information onto at least one region in the ultrasound image of the object.

2. The ultrasound diagnosis apparatus of claim 1, wherein the controller recognizes the object by comparing the ultrasound image of the object with at least one reference image.

3. The ultrasound diagnosis apparatus of claim 1, wherein the controller recognizes the object based on environment setting information of the ultrasound diagnosis apparatus.

4. The ultrasound diagnosis apparatus of claim 3, wherein the environment setting information of the ultrasound diagnosis apparatus comprises a type of application and a type of a probe used for acquiring the ultrasound image of the object.

5. The ultrasound diagnosis apparatus of claim 1, wherein the user interface receives an input for setting at least one region of interest (ROI) in the ultrasound image of the object and an input for selecting texture information for each of the at least one ROI from among the searched at least one piece of texture information, and
wherein the image processor performs texture mapping of the selected texture information onto each of the at least one ROI.

6. The ultrasound diagnosis apparatus of claim 1, wherein the texture information comprises at least one selected from the group consisting of color information, transparency, and a normal map.

7. The ultrasound diagnosis apparatus of claim 1, wherein the at least one piece of texture information is obtained from an external image.

8. The ultrasound diagnosis apparatus of claim 1, wherein the controller is configured to search the at least one piece of texture information based on an input for setting the texture information and the identified type of the object.

9. The ultrasound diagnosis apparatus of claim 1, further comprising a memory configured to store the texture information.

10. The ultrasound diagnosis apparatus of claim 9, wherein, if new texture information is added, or the stored at least one piece of texture information is edited or deleted, the controller updates the at least one piece of texture information by reflecting the addition, edit, or deletion, and
wherein the memory stores the updated at least one piece of texture information.

11. The ultrasound diagnosis apparatus of claim 1, wherein the image processor reflects at least one selected from the group consisting of effects of an external light source, reflected light, and shade on the object, thereby performing texture mapping of selected piece of texture information onto the at least one region in the ultrasound image of the object.

12. The ultrasound diagnosis apparatus of claim 1, wherein the image processor performs texture mapping of the selected piece of texture information onto the at least one region in the ultrasound image of the object, based on surface rendering or volume rendering.

13. The ultrasound diagnosis apparatus of claim 1, further comprising a probe configured to transmit an ultrasound signal to the object and receive an echo signal reflected from the object.

14. An ultrasound diagnosis method, comprising:
recognizing, by a controller, an object shown in an ultrasound image based on an input for selecting the object shown in the ultrasound image from among a plurality of objects;
identifying, by the controller, a type of the recognized object from among a set of types of a set of objects;
searching, by the controller, at least one piece of texture information corresponding to the identified type of the object from among a set of pieces of texture information corresponding to the set of objects;
displaying, by a display, the ultrasound image and the searched at least one piece of texture information corresponding to the identified type of the object;
receiving, by a user interface, an input for selecting one piece of texture information from among the searched at least one piece of texture information; and
performing, by an image processor, texture mapping of the selected piece of texture information onto at least one region in the ultrasound image of the object.

15. The ultrasound diagnosis method of claim 14, wherein the object is recognized by comparing the ultrasound image of the object with at least one reference image.

16. The ultrasound diagnosis method of claim 14, wherein the object is recognized based on environment setting information of an ultrasound diagnosis apparatus.

17. The ultrasound diagnosis method of claim 16, wherein the environment setting information of an ultrasound diagnosis apparatus comprises a type of application and a type of a probe used for acquiring the ultrasound image of the object.

18. A non-transitory computer-readable recording medium having recorded thereon a program for executing the method of claim 14 on a computer.

* * * * *